United States Patent [19]

Long et al.

[11] 4,066,679

[45] Jan. 3, 1978

[54] BIMETALLIC SALTS AND DERIVATIVES THEREOF, THEIR PREPARATION AND USE IN THE COMPLEXING OF LIGANDS

[75] Inventors: Robert B. Long, Atlantic Highlands; Fred A. Caruso, Elizabeth, both of N.J.; Richard J. DeFeo, Baton Rouge, La.; David G. Walker, Baytown, Tex.

[73] Assignee: Exxon Research & Engineering Co., Linden, N.J.

[21] Appl. No.: 557,494

[22] Filed: Mar. 12, 1975

Related U.S. Application Data

[62] Division of Ser. No. 144,302, May 17, 1971, Pat. No. 3,887,600, which is a division of Ser. No. 805,912, Sept. 3, 1968, Pat. No. 3,651,159.

[51] Int. Cl.$^2$ ................................................ C07F 1/08
[52] U.S. Cl. ............................ 260/438.1; 260/679 A
[58] Field of Search ...................... 260/438.1; 423/246, 423/247

[56] References Cited

U.S. PATENT DOCUMENTS

| 3,420,862 | 1/1969 | Long | 260/438.1 |
| 3,440,296 | 4/1969 | Walker | 260/438.1 |
| 3,592,865 | 7/1971 | Long et al. | 260/677 A |
| 3,647,843 | 3/1972 | Walker et al. | 260/438.1 |

OTHER PUBLICATIONS

Chemical Abstracts 75, 38570x (1971).
Turner et al., JACS 88, p. 1877 (1966).
Turner et al., JACS 85, 4046–4047 (1963).

*Primary Examiner*—Helen M. S. Sneed
*Attorney, Agent, or Firm*—J. Simon; C. Leon Kim

[57] ABSTRACT

Bimetallic salts, having the generic formula $MM'X_n$ wherein M is a Group IB metal, M' is a Group IIIA metal, X is a halide and $n$ is equal to the sum of the valences of M and M', are prepared by reacting the halogen salts of the individual metals, M and M', in a suitable solvent. The bimetallic salt formed thereby is a discrete monomeric species and can be utilized in the separation and recovery of various ligands, by preferential complexation. Complexation can be conducted with the bimetallic salt in the solid state, in solution, or as a slurry, and with the complexible ligand in the gaseous or liquid state. The ligand is recovered by decomplexation of the bimetallic salt-ligand complex or by displacement of the complexed ligand with another ligand.

10 Claims, 1 Drawing Figure

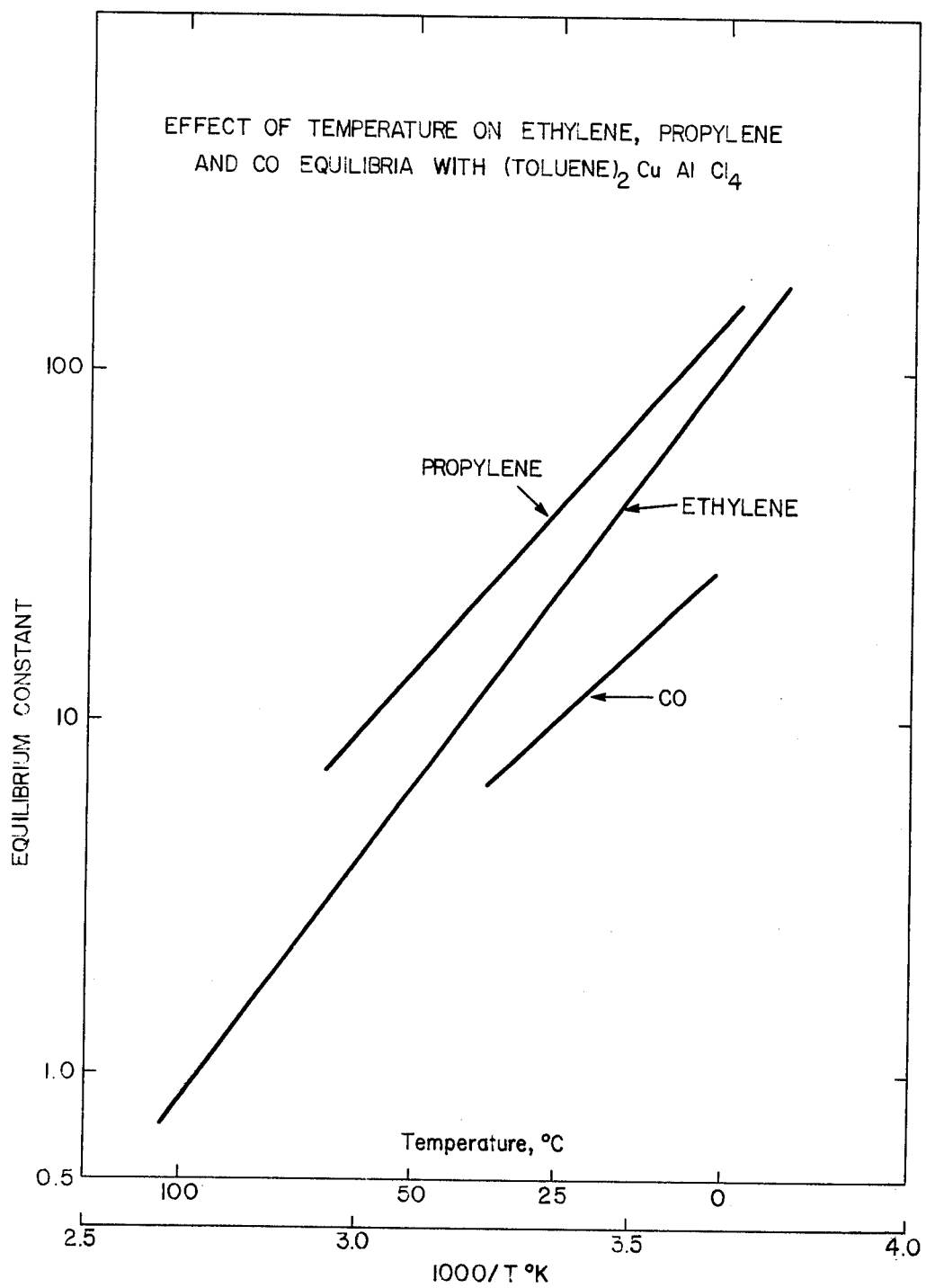

BIMETALLIC SALTS AND DERIVATIVES THEREOF, THEIR PREPARATION AND USE IN THE COMPLEXING OF LIGANDS

This a division of application Ser. No. 144,302 filed May 17, 1971 now U.S. Pat. No. 3,887,600 which in turn is a division of Ser. No. 805,912 filed Sept. 3, 1968 now U.S. Pat. No. 3,651,159.

FIELD OF THE INVENTION

This invention relates to the preparation and use of novel monomeric bimetallic salts having the generic formula $MM'X_n$ wherein M is a Group IB metal, M' is a Group IIIA metal, X is a halide, and $n$ is equal to the sum of the valences of M and M'. More particularly, this invention relates to the use of these novel salts in the separation and recovery, by preferential complexation, of various ligands, i.e., electron donors. In another embodiment hereof, this invention relates to the preparation and use of novel complexes of these bimetallic salts having the generic formula $MM'X_nL_m$ wherein M, M', X, and $n$ are as described, L is a ligand, e.g., a hydrocarbon, and $m$ is equal to the complexing stoichiometry of L and is an integer from 1-4.

PRIOR ART

The use of various salts as sorbents (complexing agents) for the separation and recovery, i.e., purification, of various ligands is well known to the art. Such salts as cuprous ammonium acetate and cuprous halides, e.g., cuprous chloride, have been widely employed to recover ligands such as acetylenes, butadiene, carbon monoxide, monoolefins, etc. While the use of such salts has generally been successful, several disadvantages are associated with their use. Thus, the salts, particularly the cuprous ammonium acetate, do not have wide applicability and have been useful in recovering only a few different ligands. The cuprous halides, although possessing the ability to recover several types of ligands, necessitate the use of rather severe conditions. To illustrate, cuprous chloride has been found useful for complexing ethylene, e.g., as from ethane/ethylene streams. However, because the ethylene-cuprous chloride complex is relatively unstable, i.e., has a high dissociation pressure, at room temperatures and atmospheric conditions, it is necessary to employ low temperatures and/or high pressures to make ethylene recovery feasible. Thus, at atmospheric pressure, ethylene complexing starts at 16° F. and at 0° F. only a 44 wt.% recovery from 50 wt. % ethylene streams can be obtained. Now, since commercial operations require better than a 90 wt. % recovery, temperatures must be in the range of −35° F. to −80° F. with several hundred psi pressure to achieve such results. Obviously, compression and/or refrigeration costs greatly increase the cost of producing ethylene in this manner.

It has now been found, however, that ethylene recovery, for example, in excess of 90 wt. %, preferably in excess of 95 wt. %, more preferably in excess of 99 wt. %, e.g., 99.9 wt. %, can be achieved at room temperature and ambient pressures and that the purity of ethylene so recovered will be in excess of 99 wt. %, when the invention to be described herein is utilized. Moreover, this invention provides a sorbent that is more versatile than those previously in use, i.e., it is applicable to a wide variety of ligands, has a greater capacity for sorbing ligands, and generally overcomes all of the shortcomings of prior art sorbents.

As used herein, the term "ligand" is defined as a complexible molecule, generally an unsaturated compound, capable of donating a pair of electrons and capable of forming a coordinating bond with a metal, M, as in $2(CH_3-CH=CH_2).CuAlCl_4$ where the two propylene molecules are coordinated to the copper atom. Also, the term "complex" as used herein is meant to include adsorption as well as absorption and the product formed thereby, the process generally being referred to as sorption wherein a sorbent (salt) sorbs (complexes) a sorbate (ligand) and the complex may then be desorbed (decomplexed).

SUMMARY OF THE INVENTION

In accordance with this invention, therefore, monomeric bimetallic salts having the formula $MM'X_n$ wherein M is a Group IB metal, M' is a Group IIIA metal, X is a halide, and $n$ is equal to the sum of the valences of M and M', are prepared by reacting the respective halides of M and M', the halide of M preferably being present in an excess, in the presence of a suitable reaction medium, generally a solvent for the Group IIIA metal halide. The monomeric bimetallic salt can then be easily recovered, e.g., by driving off the solvent and/or filtering away excess Group IB salt, and utilized in the sorption of various ligands, such as acetylene, monoolefins, polyolefins, conjugated diolefins, aromatics, cyclic olefins, carbon monoxide, etc., and generally those compounds designated as ligands.

The bimetallic salts prepared in accordance herewith are discrete monomeric species and are to be distinguished from the crystalline, polymeric materials reported by Amma, JACS, 85, 4046 (1963), and Turner and Amma, JACS, 88, 1877 (1966). These references report the formation of crystalline structures made up of infinite zigzagging sheets composed of tetrahedral $Cu(I)^+$ and $AlCl_4^-$, the structure being reported in the former article as:

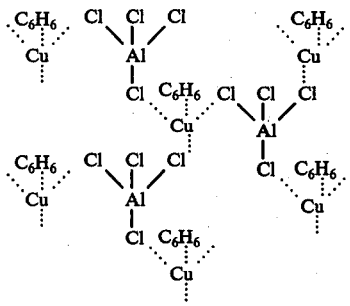

Thus, the $Cu(I)^+$ ion is bonded to Cl atoms of three different $AlCl_4^-$ tetrahedra and a benzene ring making the $Cu(I)^+$ ion four coordinate. The latter article further supports this structure and presents X-ray data to prove that the complex forms pleated crystalline sheets with adjacent sheets being held together by van der Waals' forces.

From an examination of the structure reported in the literature, it is readily apparent that the benzene to Cu(I) mole ratio is 1:1 throughout the polymeric structure and the generic formula for such a polymer can be written as $(C_6H_6.CuAlCl_4)_n$ wherein $n$ represents a number much greater than one. It is believed that the crystalline polymer reported resulted from the manner in which it was prepared, i.e., in an evacuated system using dry benzene and anhydrous resublimed cuprous chloride and anhydrous resublimed aluminum chloride. Nevertheless, the procedure utilized herein, i.e., reacting halides of M and M' in a suitable solvent such as an aromatic, gives rise to a structure believed to be a discrete monomeric species which can be pictured as having the structural formula:

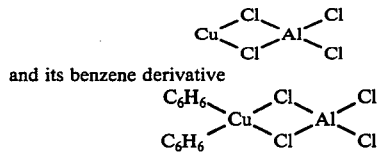

and its benzene derivative $$\begin{array}{c} C_6H_6 \\ C_6H_6 \end{array} Cu \begin{array}{c} Cl \\ Cl \end{array} Al \begin{array}{c} Cl \\ Cl \end{array} \qquad II.$$

From formula II it is apparent that the benzene to Cu(I) mole ratio is 2:1 and that the generic formula can be written as $(C_6H_6)_2CuAlCl_4$, which is structurally far different from that reported by Amma. Moreover, an examination of the two structures reveals that the Cu(I) of Amma is bonded to three separate Al through Cl bridges, whereas the structure of formula II shows the Cu(I) bonded to but one Al through only two Cl bridges. Clearly, then, a different structure having rather different properties is reported herein, e.g., in the complexing of aromatics such as benzene a 100% increase in stoichiometry over the Amma structure can be obtained.

The difference is preparative technique which is believed to account for the difference in structure and properties reported herein is believed to be due to the codissolving, with reaction, of the respective metal halides in a stoichiometric amount of, for example, an aromatic such as benzene, such that two moles of aromatic as present for each mole of bimetallic salt (see formula II). A clear solution is obtained which contains no free, i.e., unbonded, aromatic, and which chemically analyzes for $(Aromatic)_2.MM'X_n$. This structure is evidenced by data obtained from chemical analysis of stoichiometry and nuclear magnetic resonance (NMR) studies. Thus, after exchanging the aromatic complex with propylene, NMR studies of a (Propylene)$_2$-.CuAlCl$_4$ sample showed that the Al was tetrahedrally bound to four Cl atoms and that two propylene molecules were complexed.

The invention described herein has several distinct advantages over prior art complexing agents such as CuCl in that (1) a wide variety of ligands can be complexed at ambient conditions, due to the stabilizing influence of the Group IIIA metal salt; (2) ligand to copper mole ratios in excess of 1:1 can be achieved, whereas CuCl could carry only one mole of monoolefin or one-half mole of diolefin per mole of copper; and (3) aromatics can be complexed whereas prior art compounds were capable of complexing only aliphatic hydrocarbons.

The monomeric bimetallic salts have been described herein as having the generic formula $MM'X_n$. Thus, M is a Group IB metal, i.e., copper, silver, or gold, copper (I) being particularly preferred. M' is a Group IIIA metal, i.e., boron, aluminum, gallium, indium, thallium, while boron and aluminum are preferred, aluminum being particularly preferred. X is a halide, i.e., fluoride, chloride, bromide, iodide, and chlorine and bromine are preferred, particularly chlorine. The most preferred bimetallic salts are $CuAlCl_4$ and $CuAlBr_4$, particularly the chloride derivative, while other representative salts are $CuBF_4$, $CuBCl_4$, $AgBF_4$, $AgBCl_4$, $AgAlCl_4$, $AgAlBr_4$, $CuGaCl_4$, $CuInCl_4$, $CuThCl_4$, and the like.

The monomeric bimetallic salts of this invention are readily prepared by reacting the respective halides of M and M' in a suitable reaction medium. Since the bimetallic salt will generally be soluble, to some extent, in the same solvents as the Group IIIA metal salt, it is preferred to employ as a reaction medium, a solvent in which one of the salts of either M or M' is soluble or partially soluble and the other is insoluble or relatively insoluble. Thus, Group IIIA metal halides, such as $AlCl_3$, are generally soluble in aromatics, e.g., $C_6$–$C_{20}$ aromatics, preferably $C_6$–$C_{12}$, more preferably $C_6$–$C_9$ aromatics such as benzene, toluene, xylene, mesitylene, and most preferably toluene. On the other hand, Group IB metal halides, such as CuCl, are soluble in $C_2$–$C_{20}$ monoolefins, preferably $C_2$–$C_9$, more preferably $C_4$–$C_9$ monoolefins, e.g., ethylene, propylene, isobutylene, butenes, hexenes, heptenes, and the like, most preferably alpha monoolefins. Aromatic solvents, however, are most advantageously utilized.

Of course, other components may also be present during the reaction so long as a solvent in which one salt is relatively soluble and the other is relatively insoluble is present, and two such solvents may be present, e.g., reacting a solution of CuCl in a monoolefin and a solution of $AlCl_3$ in an aromatic. Now, since the bimetallic salt will complex with a variety of compounds, including such compounds, i.e., ligands, as aromatics and monoolefins, a complex having the greatest stability will form, and, in this instance, the monoolefin complex being more stable than an aromatic complex will form.

Other illustrative preparative techniques that may be employed involve contacting solid CuCl with an aromatic solution of $AlCl_3$, thereby forming a solution of $CuAlCl_4$.$(Aromatic)_2$ complex in the aromatic; contacting CuCl slurried in a paraffin, e.g., a $C_5$–$C_{20}$ paraffin, with an aromatic solution of $AlCl_3$; contacting solid $AlCl_3$ or $AlCl_3$ slurry with a solution of CuCl in a monoolefin, thereby forming a precipitate or solution of $CuAlCl_4$.$(Monoolefin)_2$; and any other combination that may be desirable under the circumstances. Preferably, the solvent is employed in a stoichiometric relationship to the bimetallic salt product. Thus, for aromatics and monoolefins, such as ethylene or propylene, the stoichiometric relationship can be one or two, preferably two, and, therefore, two moles of solvent are then employed for each mole of cuprous chloride and aluminum chloride utilized.

The complex may then be recovered, e.g., by filtering, decanting, etc. the precipitated $CuAlCl_4$.$(Olefin)_2$ complex, or driving off excess solvent from $CuAlCl_4$.$(Aromatic)_2$ and soluble $CuAlCl_4$.$(Olefin)_2$ complexes and the bimetallic salt obtained by decomplexing the complex, e.g., by heat and/or reduced pressure. A typical preparation technique is illustrated herein as (Ar = Aromatic, S = Solid, Sl = Slurry, L = Liquid):

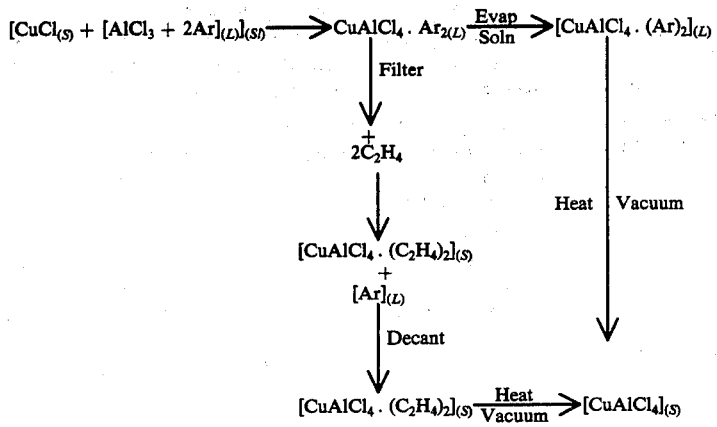

The conditions under which the bimetallic salt is prepared are generally not critical and may vary widely. It is only necessary that the system be in the liquid state, i.e., the solvent is maintained in the liquid state, above the freezing point and below the boiling point of the particular solvent utilized. Thus, temperatures under which the respective M and M' halides can be contacted can range from about −40° to 300° F. These temperatures are practical limits since below about −40° F. most of the preferred aromatic solvents, or their complexes, tend to solidify while above about 300° F. the most preferred $C_6$–$C_8$ aromatics tend to boil, unless preparation is carried out above atmospheric pressure. Preferably, temperatures range from about 0° to 150° F. Pressures, too, may vary and subatmospheric as well as superatmospheric pressures can be employed, for example, 0.1 to 1000 psi, preferably atmospheric to 100 psi. However, conditions of room temperature, i.e., 18°–25° C. and atmospheric pressure can be advantageously employed.

One factor of considerable importance in the preparation of these novel salts relates to the catalytic activity of free Group IIIA metal salts such as the highly active Friedel-Crafts catalyst $AlCl_3$. In order to eliminate free $AlCl_3$, for example, an excess of the Group IB salt is preferably employed, thereby insuring that all the $AlCl_3$ reacts. It is only necessary that some excess Group IB salt is present; however, preferably, the molar ratio of Group IB metal salt/Group IIIA metal salt is at least 1.01, and more preferably ranges from about 1.02 to 1.2. Additional Group IB metal salt could be employed but this would generally lead to excess solids in the reaction medium, when an aromatic solvent is employed, and these would only have to be removed, e.g., by filtration. This procedure generally inhibits or neutralizes catalytic activity of the sorbent for all but the most reactive of compounds, e.g., higher monoolefins or diolefins.

The starting materials utilized for the reaction should be of substantial purity, e.g., 99+% pure. Thus, recrystallized CuCl can be employed and $AlCl_3$ can be purified by heating while fluidizing with nitrogen and blowing out any HCl or $H_2O$ that may be present. Further, the halides should be stored in the absence of oxygen and water which tend to oxidize and hydrolyze the components, respectively. Similarly, the reaction to form the bimetallic salt and any reactions (sorbing processes) in which the bimetallic salt is employed should preferably be run under substantially anhydrous conditions and in the substantial absence of oxygen. Generally, however, water and oxygen can be present in amounts similar to that tolerated by Ziegler type catalysts, e.g., less than about 10 ppm water or oxygen. Additionally, the solvent selected for preparing the bimetallic salt should not be capable of being polymerized by the Group IIIA metal halide and only inert reaction media should be employed. Thus, aromatic solvents are far more preferred than monoolefinic solvents.

The novel bimetallic salts or their derivatives, e.g., $CaAlCl_4$.(Aromatic)$_2$, are quite useful in the sorption and separation and recovery, in highly concentrated forms, of various ligands. The salts are quite versatile and may be employed as solutions (in aromatics) or as liquid complexes of $CuAlCl_4$.(Aromatic)$_2$, as a solid (fluidized or fixed bed), or as slurries (in paraffins with or without aromatic activators) and can be contacted with ligands wherein the ligand can be in either the gaseous or liquid states. Thus, it is only necessary that the salt and the ligand be placed in intimate contact and this is readily achieved by normal gas-solid, gas-liquid, liquid-solid, liquid-liquid contacting means. However, it is generally preferred to take advantage of the physical state of the ligand in fixing the contacting means. Thus, if the ligand is gaseous, the sorbent is generally liquid, and, if the ligand is liquid, the sorbent may be liquid or solid. It is noted generally that when the sorbent is employed as a solid, the ligand recovery is increased as the temperature of the ligand approaches its dew point, that is, a ligand should be within 30° F. of its dew point, preferably within 20° F., more preferably within 10° F. of its dew point, with these temperatures above the dew point when utilizing a solid bimetallic sorbent.

A wide variety of ligands can be complexed, i.e., sorbed, by these novel bimetallic salts. Among these are unsaturated compounds such as olefins, acetylenes, aromatics, carbon monoxide, and the like. More specifically, the unsaturated hydrocarbons can be (a) acetylenes, such as $C_2$–$C_6$ acetylenes, preferably $C_2$–$C_4$ acetylenes, e.g., acetylene, methyl acetylene, ethyl acetylene, dimethyl acetylene, vinyl acetylene, etc.; (b) monoolefins, such as $C_2$–$C_{20}$ monoolefins, preferably $C_2$–$C_{10}$, more preferably $C_2$–$C_5$ monoolefins, most particularly ethylene and propylene; (c) conjugated diolefins, such as $C_4$–$C_{10}$ conjugated diolefins preferably $C_3$–$C_6$ conjugated diolefins, e.g., butadiene, isoprene, etc.; (d) polyolefins, such as $C_6$–$C_{16}$, preferably $C_6$–$C_{12}$ polyolefins, e.g., cyclododecatriene, cyclooctadiene; (e) cyclic olefins and alicyclic olefins, such as $C_5$–$C_{10}$, preferably $C_6$–$C_8$, e.g., cyclopentene, cyclohexene, cyclooctene, etc.; (f) aromatics, such as $C_6$–$C_{12}$ aromatics, preferably $C_6$–$C_8$ aromatics, e.g., benzene, xylene, toluene; and (g) cumulative diolefins, such as $C_3$–$C_6$ cumulative diolefins, e.g., allene. The process is particularly applicable to sorbing $C_2$–$C_4$ monoolefins, $C_2$–$C_4$ acetylenes, carbon monoxide, and $C_6$–$C_9$ aromatics. Any of the foregoing ligands can be sorbed by the salt itself, while derivatives thereof, e.g., $CuAlCl_4 \cdot (Aromatic)_2$, will sorb any ligand having a greater complex stability, i.e., an exchange reaction will occur, the more stable ligand displacing the less stable ligand.

Generally, the compound to be sorbed, i.e., separated by preferentail complexation, and recovered is contained in a feed stream admixed with various other compounds which are either not sorbed or less preferentially sorbed, i.e., their complexes are less stable than the complex of the compound to be preferentially sorbed. For example, such feed streams as ethane/ethylene or propane/propylene (the paraffin not being sorbed) can be treated to concentrate the olefin. In cases, however, where several ligands can be sorbed, e.g., when a solid sorbent or slurry is employed, the complexed ligands can be decomplexed as a whole, or individually, and recovered by distillation or fractional decomplexing, respectively.

While the stability of various complexes will vary widely, it can generally be stated that monoolefin complexes are more stable than acetylene complexes which, in turn, are more stable than carbon monoxide complexes which, in turn, are more stable than aromatic complexes. In monoolefin complexes, propylene complexes are more stable than ethylene complexes, and stability is believed to be related to molecular weight. Because of the wide range of ligands available for complexing, it is understood that several compounds of each class mentioned herein will overlap compounds of other classes. Nevertheless, one skilled in the art can readily determine, by routine experimentation, the exact order of stability fo any set of complexes.

The bimetallic salt can be used as a dry solid, in a slurry with diluents such a $C_3$–$C_{20}$ paraffins, $C_5$–$C_{20}$ naphthenes, or as a solution in $C_6$–$C_{12}$ aromatics of $C_5$–$C_{12}$ cycloolefins. Of course, when aromatic solutions are employed, the aromatic solutions are employed, the aromatic complex is believed to form (and the sorbent is then the aromatic complex rather than the salt alone), but since the aromatic complex is the least stable relative to the various other complexible ligands, the aromatic is readily displaced by the desired ligand, and the aromatic complex is a preferred sorbing because it is a liquid sorbent. Each of the sorbing techniques mentioned has advantages and disadvantages regarding its use. For example, the complexing of ethylene with $CuAlCl_4$ as a dry solid or a paraffin slurry gives an invariant equilibrium constant while the use of a toluene or other aromatic solution or liquid aromatic complex of $CuAlCl_4$ gives a solution equilibrium which depnds upon the amount of reactants and products present. The invariant equilibrium has the advantage the permitting all of the $CuAlCl_4$ to be consumed in the process while the solution type equilibrium limits conversion by the formation of free aromatic (by displacement) and the comsumption of the $(Aromatic)_2 \cdot CuAlCl_4$ complex. On the other hand, product yield is limited by the dissociation pressure of the $(Ethylene)_2 \cdot CuAlCl_4$ complex in the invariant case whereas complete product recovery can be obtained in the solution case. It is generally preferred, however, to employ aromatic solutions, i.e., liquid aromatic complexes, (because of their ease in handling, e.g., heat of complexation is readily dissipated both because it is balanced in ligand exchange and because of easier heat transfer, intimate contact between ligand and sorbent is promoted) of the bimetallic salt or paraffin slurries activated with at least about 10 mole %, preferably about 10 to about 300 mole % aromatic, more preferably 100 to 150 mole % aromatic based on the bimetallic halide salt, the aromatics being those previously described as useful for solution preparation. It is believed that activation involves solution of the bimetallic salt by the activator, e.g., $C_6$–$C_8$ aromatics, and increasing amounts of activator will increase the solution of salt. Thus, the use of a slurry with an aromatic activator will approach, in operation and result, the use of an aromatic solution or liquid aromatic complex as the amount of activator increases.

It is interesting to note that the number of moles of ligand per mole of copper in the bimetallic salt increases from 1:1 to 2:1, for example, in monoolefin complexes, as the system is changed from dry solid or paraffin slurry to aromatic solution or aromatic activated slurry and, therefore, the recovery of ligand is increased. This variable capacity of the salt with regard to ligands is an interesting phenomenon attendant to this invention. While the theoretical nature of this phenomenon is not yet understood, it has been determined that the complexing stoichiometry, i.e., the number of moles of ligand that will complex with one mole of bimetallic salt varies, depending upon the reaction phase, e.g., liquid sorbent, solid sorbent, and the physical state of the ligand, e.g., liquid, gas. Thus, the generic formula of the complexes formed by ligands and the bimetallic salt may be represented as $MM'X_nL_m$ wherein M, M', X, and n have been previously described, L is a complexible ligand as described, and m is equal to the complexing stoichiometry of the ligand and is an integer from 1 to 4. Now, since the ligands are coordinated to the M metal, e.g., Cu(I), and M has a maximum coordination number of 4, the maximum of m must be 4. The most common form of coordination of M, however, ranges from 1 to 2 (an m of 2 is shown above in formula II). Generally, for aromatics and monoolefins, m is 1 to 2, usually 2; for example, 1 when only 1 mole of aromatic is used to form the complex; for carbon monoxide and acetylene, m is usually 1, and for cumulative olefins such as allene, m is usually 1.

While in many instwances herein m is shown as 2, it is believed that as the system becomes increasingly ionic, for as yet unknown reasons, one of the bonds between Cu(I) and Cl is broken, thereby allowing another ligand to complex with Cu(I), such as:

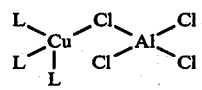     III.

and in a completely ionic system where an $[AlCl_4]-$ ion and a $[CuL_4]+$ ion is present, the structure would be:

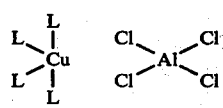     IV.

which shows the breaking of both Cu(I) to Cl bonds. Again, while it is apparent that $m$ may vary from 1 to 4, depending upon the nature of the systems, little is known about the theoretical aspects of this variation. However, it is conceivable that ligand driving force may also play a role in this phenomenon and that the physical state of the ligand and sorbent may affect that driving force.

It is also noted that in the generic formula $MM'X_nL_m$, L may be the same or different. For example, an aromatic complex, such as $(C_6H_6)_2 \cdot CuAlCl_4$ can be treated with one mole of ethylene, which is a stronger complexing agent than benzene, thusly:

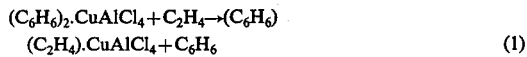
(1)

and treatment with another mole of ethylene yielding:

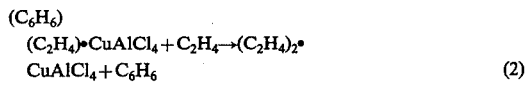
(2)

the overall equation being written as:

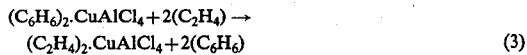
(3)

Obviously, then a variety of complexes can be formed, depending upon the relative stability of ligands and treatment ratios. Additionally, the foregoing expressions also illustrate a displacement reaction which can be utilized to recover ligands. As will be discussed hereinbelow, these displacement reactions can be made reversible so as to aid in the recovery of a variety of ligands.

One of the particular advantages of this process is that ligand recoveries can be obtained at reasonable conditions. Thus, while somewhat different conditions for complexing and decomplexing will apply for different materials, conditions are generally not critical and may vary widely. Thus, for any type of complexing, reaction temperatures may range from about −40° F. to about 300° F., preferably −40° F. to 200° F., and more preferably about 50° F. to 150° F. Pressures similarly may vary widely and can range from about 0.5 atmosphere to about 100 atmospheres, preferably 1 to 20 atmospheres. While decomplexing to recover a desired ligand may be carried out in a variety of ways, e.g., dissociation, displacement, decomplexing by dissociation will occur at a temperature higher than complexing (for constant pressure processes) and in the range of about 50° F. to about 500° F., preferably about 200° F. to 400° F., or at lower pressures than for complexing (for constant temperature processes) and in the range of about 0.1 to 30 atmospheres, preferably 0.5 to 20 atmospheres. Most preferably, however, liquid sorbent systems are employed, and still more preferably liquid sorbent systems with gaseous ligands are employed. In these most preferred systems, the same general conditions as already outlined will apply; however, liquid systems are only limited by those conditions under which the ligand remains liquid.

Additionally, the complexed ligand can be used as a storage device for that ligand. For example, in the case of carbon monoxide or other low boiling ligands, storage is generally effected in pressure vessels as a gas or in cryogenic containers as a liquid. In either case, rather expensive storage devices are required which are relatively hazardous, e.g., high pressures, or may result in large losses if a leak in a liquid system develops. Moreover, so long as the bimetallic salt is fully complexed, there is no danger of contamination in storage and an exceedingly high purity product can be stored and transported relatively easily. Further, higher molecular weight ligands, such as aromatics, can now be stored as solids at relatively high temperatures and also can be kept for long periods in an exceedingly high state of purity.

The recovery of the complexed ligand can be effected in a variety of ways depending upon the sorbent system that is employed. For example, in a solution system, using $CuAlCl_4 \cdot (Aromatic)_2$, for example, some monoolefin complexes will precipitate, e.g., the ethylene complex, and can be recovered by filtration, decantation, centrifugation, etc. Filtration, etc. can also be employed to recover such complexes from slurry systems. After separation of the complex, it can be decomplexed by heating in the presence of an inert stripping gas, e.g., nitrogen, helium, argon, carbon dioxide, and the ligand then is easily separated from the stripping gas, e.g., by condensation, distillation, etc., and the salt and slurry diluent are then recycled to the process. Obviously, the stripping gas could also be a boiling aromatic.

Another recovery method, which readily lends itself to continuous operations involves reversible displacement reactions for solution type sorbent systems, i.e., use of aromatic solvents for bimetallic salt. Such displacement reactions may be readily exemplified by the following expressions which show the recovery of propylene using a toluene complex:

Complexing:

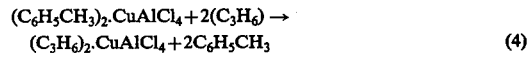
(4)

Displacement:

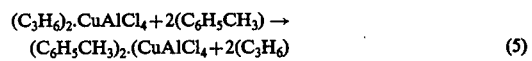
(5)

In equation (4) a liquid aromatic complex can be employed to recover liquid or gaseous monoolefin from a feed stream containing propane and propylene, for example. The resulting monoolefin complex is soluble in the liquid medium formed by liberation of liquid toluene, gaseous propane bubbling through unaffected since propane does not complex. The propylene can be recovered by heating to shift the equilibrium and stripping with inert gas or boiling toluene, equation (5), under conditions, i.e., higher temperature and/or lower pressure, which will favor the reverse reaction. Thus, equations (4) and (5) may be written as a single reversible equation. FIG. 1, attached hereto, is a log plot of equilibrium constant against temperature at constant atmospheric pressure for the reversible complexation of several ligands with a $(Toluene)_2 \cdot CuAlCl_4$ complex. In this plot, by operating at lower temperatures, the products will increase, i.e., complexes of ethylene, propylene, or CO will tend to form at the expense of the toluene complex. The opposite is true for operation at higher temperatures.

As previously discussed, the use of an excess of Group IB metal halide insures the reaction of all of the Group IIIA metal halides and, therefore, substantially neutralizes the catalytic activity, e.g., alkylation, polymerization, of the Group IIIA salts. Nevertheless, the bimetallic salt may contain some residual catalytic activity due to the acid nature imparted to it by the Group IIIA salt. This residual activity generally will only appear when highly reactive ligands, e.g., diolefins, such as butadiene, or $C_3+$ monoolefins such as hexane, heptene, etc., are utilized in the sorption process. Moreover, this catalytic activity is further promoted when such reactive ligands are decomplexed by heating at high temperatures which can cause catalytic polymerization or alkylation of the desired ligand. In such cases, it is advisable to employ recovery methods such as displacement or decomplexation using pressure changes rather than using increased temperatures for decomplexation. Nevertheless, this residual catalytic activity (or acidity) can be effectively neutralized after preparation of the bimetallic salt by the use of certain additives, i.e., neutralizing agents. These neutralizing agents are generally characterized as basic materials, and are exemplified by ammonia and organic nitrogen bases which preferably have a boiling point in the same range as the reaction solvent (if a solvent is employed) so as to insure the presence of the neutralizing agent under all reaction conditions. Examples of such organic nitrogen bases are aniline, pyridine, quinoline, trimethylamine, triethylamines, tri-n-butylamine, and the like, and $C_1$-$C_{10}$ nitrogen bases generally. Additionally, Group VB metal trihalides can be effectively employed as neutralizing agents, e.g., antimony trichloride, phosphorous trichloride, arsenic trichloride, tribromide derivatives, etc. Under normal circumstances, it is only necessary that small amounts of neutralizing agent be present, e.g., merely enought to react with free acidity of the system. In fact, the presence of too much neutralizing agent causes precipitation of copper salt from the solution leading to formation of a different catalytic species. Preferably, the neutralizing agent is present in an amount of at least about 0.01 wt. % based on sorbent, more preferably about 0.1 wt. %. Preferred materials are ammonia and pyridine which are preferably employed with aromatic sorbent solutions in amounts ranging from about 0.01-1 wt. % based on sorbent. (The neutralizing agents described herein can also be employed in a like manner during the preparation of the bimetallic salt when $C_3+$ monoolefinic solvents are employed.)

Having now described the invention, the following examples will further serve to illustrate the preparation and use of these novel bimetallic salts. However, no limitations are to be implied from these examples since variations and modifications will be obvious to those skilled in the art.

EXAMPLE 1

1.1 moles of carefully purified CuCl (109 grams) were mixed with 1 mole of purified $AlCl_3$ (133 grams) in an inert nitrogen atmosphere as dry powders. This powder was slowly added with agitation in an inert atmosphere to 2 moles (156 grams) of dry benzene. The mixture was allowed to stir for one hour. The clear, dark liquid was removed from the small quantity of undissolved solids by decantation. The liquid was then treated with anhydrous ethylene gas, and a solid ethylene complex was formed. The solid was separated by filtration, and washed with pentane saturated with ethylene. The solid was dried in a stream of ethylene. The dry solid was then heated in a vacuum, and the ethylene was decomplexed yielding the free $CuAlCl_4$. Elemental analysis of the ethylene complex before decomposition showed:

| Calculated: | Cu 22.0 | Al 9.4 | Cl 49.1 | C 16.7 | H 2.8 |
|---|---|---|---|---|---|
| Found: | Cu 21.0 | Al 9.7 | Cl 53.2 | C 17.1 | H 3.1 |

This analysis corresponds to $CuAlCl_4 \cdot 2(C_2H_4)$ and shows a 2:1 complex, indicating that the original benzene complex was a 2:1 complex.

EXAMPLE 2

Various ligands were recovered using a solution sorbent system of $CuAlCl_4$ in toluene prepared by dissolving 232 grams of $CuAlCl_4$ prepared similarly as in Example 1 in 184 grams toluene. The ligand feed streams were fed into solution as vapors by allowing the feed stream to bubble through the liquid and the complexed ligand recovered by heating the complex to the boiling point of the complex. Table I shows the results of this experiment.

TABLE I

| Feed | Methyl Acetylene/Propane | Allene/Propane |
|---|---|---|
| Complexed Ligand | Methyl Acetylene | Allene |
| Temperature, ° C. | 23 | 25 |
| Pressure, psig | 0 | 0 |
| Ligand Content, Mole % | | |
| Feed | 49 | 45 |
| Initial Tail Gas | 0.13 | 1.4 |
| Decomplexed Product | 99.9+ | 99.9+ |

The results in this table clearly show the ability of the toluene.$CuAlCl_4$ complex to remove substantially completely the complexing ligand from the feed at room temperature and atmospheric conditions, and to produce the ligand upon decomplexing in exceedingly high purity.

EXAMPLE 3

The recovery of ethylene from an ethylene/ethane feed at room temperature and atmospheric pressure is shown in Table II using slurry, slurry-activated, and liquid aromatic complex sorbents.

TABLE II

| Complexing Agent | (Slurry) 34 Wt. % $CuAlCl_4$ in $nC_7$ | (Slurry-Activated) 29 Wt.% $CuAlCl_4$ in 3:1 $nC_7$/Toluene | 55 Wt.% $CuAlCl_4$ in Toluene Solution |
|---|---|---|---|
| Ethylene Content, Mole % | | | |
| Feed | 50 | 50 | 53 |
| Initial Tail Gas | 1.5 | 0.7 | 1.5 |
| Decomplexed Product | 99.9+ | 99.9+ | 99.9+ |
| Capacity: Moles $C_2^=$/Cu | 1 | 2 | 2 |

This table shows excellent recoveries of ethylene using any method; however, in the slurry-activated and solution sorbent systems, the amount of material necessary for complexation can be reduced, with corresponding reduction in process costs due to increased capacity of the sorbent for ethylene.

EXAMPLE 4

Table III shows the recovery of various ligands with a complex ligand sorbent system of $CuAlCl_4.(toluene)_2$.

TABLE III

| Feed | $C_2/C_2^=/C_2^-$ | $CO/CH_4/H_2$ | $C_2^=/C_3^=/C_2$ |
|---|---|---|---|
| Complexed Ligands | $C_2^=/C_2^-$ | CO | $C_2^=/C_3^=$ |
| Temp., ° C. | 24 | 25 | 27 |
| Pressure Psig | 0 | 0 | 0 |
| Ligand Content, Mole % | | | |
| Feed Initial Tail | $32.5\ C_2^=/35.6\ C_2^-$ | 32.1 | $14.5\ C_2^=/19.0\ C_3^=$ |
| Gas Decomplexed | $3.4\ C_2^=/5.5\ C_2^-$ | 5.0 | $3.2\ C_2^=/1.4\ C_3^=$ |
| Product | $65.2\ C_2^=/34.8\ C_2^-$ (100) | 100.0 (100) | $34.1\ C_2^=/65.9\ C_3^=$ (100) |

EXAMPLE 5

In some cases, the recovery of higher molecular weight olefins ($C_3+$) is accompanied by alkylation of the aromatic diluent and by polymerization of the olefin if excess catalytic acidity is present in the sorbent preparation. This example shows the use of small amounts of added nitrogen base to inhibit these side reactions.

A complexing solution was prepared by dissolving 109 grams (1.1 moles) of CuCl and 133 grams (1 mole) of $AlCl_3$ in 2 moles of toluene. Analysis of the resulting clear, dark solution showed:

| | $CuAlCl_4 . (C_7H_8)_2$ | | | | |
|---|---|---|---|---|---|
| Calculated: | C 40.3 | Al 6.5 | H 3.9 | Cl 34.1 | Cu 15.2 |
| Found: | C 39.4 | Al 6.4 | H 4.1 | Cl 34.4 | Cu 14.4 |

Portions of this solution were treated with a synthetic feed containing 50% propane and 50% propylene. One portion was treated as is, and a second was treated after addition of 0.1% anhydrous ammonia. In the case of the ammonia treated sorbent, propylene was complexed without side reactions. In the case of the untreated sorbent, side reactions accounting for over 10% of the propylene were obtained. Gas chromatographic analysis of the liquid showed the presence of alkylated aromatics and oligomers of propylene.

EXAMPLE 6

A $CuAlBr_4.(Benzene)_2$ complex was prepared by a procedure analogous to that for $CuAlCl_4.(Toluene)_2$. This solution, clear green in color, was used to separate carbon monoxide from a feed mixture containing 21% CO, 74% $H_2$, and 5% $CH_4$. Complexation was carried out at 800 psig and 25° C. The carbon monoxide was complexed selectively. At the end of the feed addition, the reactor was depressured to 0 psig, and the complex was decomposed at 60° C. to yield carbon monoxide of 99.5% purity.

EXAMPLE 7

The use of a Slurry of $CuAlCl_4$ to Complex Ethylene from an Ethylene-Ethane Mixture A slurry of $CuAlCl_4$ in heptane was prepared as follows: The $CuAlCl_4$.benzene complex was prepared by dissolving 109 grams (1.1 moles) of pure CuCl and 133 grams (1 mole) of pure $AlCl_3$ in 2 moles of benzene. The clear solution was then treated with pure ethylene to complex 2 moles of ethylene per mole of $CuAlCl_4$. This solid complex was separated from the benzene, washed with pentane, which was saturated with ethylene, and was dried in a stream of pure ethylene. The ethylene was removed from the complex by heating under vacuum, leaving pure $CuAlCl_4$. The solid was suspended in pure, dry, normal heptane such that a 50% by weight slurry was obtained. Benzene, 0.1 mole, was added as an activator.

The slurry was stirred in a well agitated reactor, and a feed stream containing 50% ethylene and 50% ethane was passed through the slurry. The ethylene was absorbed until a complex was obtained which corresponded to 2 moles of ethylene per mole of bimetallic salt. (Complexation was carried out at ambient temperature and atmospheric pressure.)

The slurry was then heated to the boiling point of the heptane diluent and the complexed ethylene was evolved in better than 99% purity. The heptane diluent was stripped from the gas by an efficient condenser. The decomplexed slurry was then capable of being returned to the complexer for another cycle.

EXAMPLE 8

Nuclear Magnetic Resonance Studies

A study was carried out of the exchange of a toluene complex of $CuAlCl_4$ to a propylene complex.

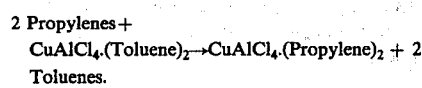

Samples were prepared in a dry box which represented the initial toluene $CuAlCl_4$ complex and 25, 50, 75, and 100% exchange with propylene. These samples were sealed in NMR tubes, and subjected to Proton NMR. The results are summarized as follows:
1. Propylene is present in increasing amount as the exchange takes place. The propylene spectra are shifted from that of pure propylene and indicate the donation of electrons.
2. The initial toluene spectra are shifted from that of free toluene and give only a single sharp peak. As the exchange takes place, this peak changes and shifts to that of free toluene so that no complexed toluene appears present at the end of the exchange.
3. The exchange data confirm that two moles of ligand are exchanged during the experiment.

EXAMPLE 9

Allene Stoichiometry

A solution of $CuAlCl_4.(Toluene)_2$ in excess toluene which contained 3.09 moles per liter of copper was used to absorb allene from a 50:50 allene-propane mixture at room temperature and atmospheric pressure. The amount of allene absorbed was calculated from analysis of the gas leaving the absorber and measurement of its volume. A total of 2.62 moles per liter of allene was absorbed corresponding to a ratio of 2.62:3.09 or 0.85 mole of allene per mole of Cu. This indicates an allene/Cu mole ratio of 1.0.

EXAMPLE 10

Ligand Exchange

Rapid ligand exchange has been demonstrated for a variety of pairs of complexing ligands. In these experiments the $(Toluene)_2 \cdot CuAlCl_4$ complex was treated at room temperature in a gas bubbler with a gas containing another ligand (either ethylene, CO, or acetylene) until the Cu would no longer pick up any of the gaseous ligand. Then a second gas containing a different complexing ligand was used to strip the solution and the exit gas was analyzed by gas chromatography. Finally, when no further changes in composition occurred, the solution was heated to 140° C. to liberate whatever was complexed on the $CuAlCl_4$. This gas was also analyzed by gas chromatography. The results are shown in the following table.

TABLE IV

| First Complexing Ligand | Ethylene | CO | Acetylene |
| --- | --- | --- | --- |
| Stripping Gas | Propylene | Ethylene | Ethylene |
| First Exit Stripping Gas | 86.7% $C_2^=$ | 90.1% CO | 82% $C_2^=$ |
| Last Exit Stripping Gas | 99.94% $C_3^=$ | 100% $C_2^=$ | 99.06% $C_2^=$ |
| Decomplexed Product | 99.97% $C_3^=$ | 99.9+% $C_2^=$ | 98% $C_2^=$ 2% $C_2^=$ |

This table shows that the first stripping gas analyzed from 82 to 90% content of the ligand which was used to form the original complex even though a different pure ligand was used as the stripping gas. This means that the few seconds needed for the gas to pass through the liquid are enough to get extensive ligand exchange. Furthermore, the very small amount of the original ligand obtained upon decomplexing shows that it was essentially completely removed by stripping with the second ligand.

EXAMPLE 11

Complexing with $CuAlBr_4$

A toluene complex of $CuAlBr_4$ was prepared by slurrying together solid CuBr and solid $AlBr_3$ in toluene at room temperature. The liquid $(Toluene)_2 \cdot CuAlCl_4$ complex formed readily and was used to recover and purify both CO and ethylene from their mixtures with non-complexing gases. Absorption was carried out at room temperature and atmospheric pressure while regeneration of the solution was carried out at 100° C. using nitrogen stripping gas.

TABLE V

| Feed Gas | 50/50 CO—$H_2$ | 50/50 Ethylene-Ethane |
| --- | --- | --- |
| Ligand Complexed | CO | Ethylene |
| Initial Tail Gas, % Ligand | 3.0 | 1.5 |
| Moles Ligand/Mole Cu | 1 | 1 |
| Purity of Decomplexed Product, % Ligand | 99.9+ | 99.9+ |

These data show that the bromine analog of $CuAlCl_4$ works about the same as the chlorine compound and can be readily prepared in aromatic solvents. Furthermore, it exchanges readily with other ligands.

What is claimed is:

1. A complex bimetallic salt having the generic formula $CuAlX_4L_m$ wherein X is selected from the group consisting of chlorine, bromine and fluorine atoms, L is a complexible ligand selected from the group consisting of a $C_2$–$C_6$ acetylene, a $C_4$–$C_{10}$ conjugated diolefin, a $C_6$–$C_{16}$ polyolefin, a $C_5$–$C_{10}$ cyclic olefin and a $C_3$–$C_6$ diolefin and m is equal to the complexing stoichiometry of L and is an integer ranging from 1 to 4.

2. A complex bimetallic salt having the generic formula $CuAlCl_4L_m$ wherein L is a $C_2$–$C_6$ acetylene and m is an integer ranging from 1 to 4.

3. The salt of claim 2 wherein L is a $C_2$–$C_6$ acetylene and m is 1.

4. The salt of claim 3 wherein L is a $C_2$–$C_4$ acetylene.

5. The salt of claim 4 wherein L is acetylene.

6. The salt of claim 4 wherein L is methyl acetylene.

7. The salt of claim 4 wherein L is ethyl acetylene.

8. A compound that has the structural formula $RC{\equiv}CH:Cu(AlCl_4)$ wherein R represents hydrogen, vinyl, ethynyl, or an alkyl group having from 1 to 10 carbon atoms.

9. The compound as set forth in claim 8 wherein R represents ethynyl.

10. The compound as set forth in claim 8 wherein R represents vinyl.

* * * * *